United States Patent [19]

Sivaramakrishnan

[11] Patent Number: 4,567,302

[45] Date of Patent: Jan. 28, 1986

[54] POLYMERIC QUATERNARY AMMONIUM SALTS POSSESSING ANTIMICROBIAL ACTIVITY AND METHODS FOR PREPARATION AND USE THEREOF

[76] Inventor: Kallidaikurichi N. Sivaramakrishnan, 4330 S. Sixth St., Terre Haute, Ind. 47802

[21] Appl. No.: 632,819

[22] Filed: Jul. 20, 1984

[51] Int. Cl.$^4$ .............................................. C07C 93/04
[52] U.S. Cl. ................................... 564/286; 564/294; 528/266; 549/371
[58] Field of Search ................ 564/286, 294; 528/266, 528/403, 405; 526/398; 424/82; 549/371

[56] References Cited

U.S. PATENT DOCUMENTS

| | | | |
|---|---|---|---|
| 2,384,607 | 9/1945 | Groote | 549/371 |
| 2,560,280 | 7/1951 | Benneville | 564/286 |
| 2,759,975 | 8/1956 | Chiddix et al. | 564/286 |
| 3,931,233 | 1/1976 | Conrad | 549/371 |
| 4,057,554 | 11/1977 | Redmore et al. | 564/286 |
| 4,198,269 | 4/1960 | Evani et al. | 528/405 |

FOREIGN PATENT DOCUMENTS

| | | | |
|---|---|---|---|
| 247017 | 4/1960 | Australia | 564/294 |
| 2362172 | 6/1975 | Fed. Rep. of Germany | 528/403 |

OTHER PUBLICATIONS

Anteunis et al., Journ. Amer. Chem. Soc., (1978), pp. 4050–4054.
Shipp et al., *J. Org. Chem.*, 31, 853, (1966).
*Polymeric Drugs*, ed. by L. Guy Donaruma et al., Academic Press, N.Y., 1978.
*Macromolecules in Solution* by H. Morawetz, Interscience Publishers, N.Y., 1965, First Edition.
*Polymer Preprints*, 22 (2), p. 393, (1981).
*Surface Active Agents & Detergents*, vol. II, Schwartz et al., Interscience Publishers, N.Y., 1958.
*J. Animal Science*, vol. 30, (1970), p. 812.

Primary Examiner—Ethel G. Love

Attorney, Agent, or Firm—Leydig, Voit & Mayer, Ltd.

[57] ABSTRACT

Quaternary ammonium salts exhibiting strong antimicrobial activity are disclosed along with the method of using them as antimicrobial agents. The salts having the formulas I or II:

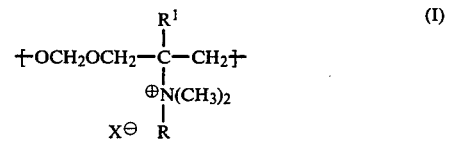

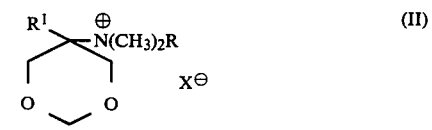

wherein R is $C_{1-20}$ alkyl, $C_{5-7}$ cycloalkyl or an aralkyl group, $R^1$ is methyl or ethyl, and X is a halogen, are prepared by the method comprising the steps of:

(a) initially reacting 2-nitro-2-methyl-1,3-propanediol or 2-nitro-2-ethyl-1,3-propanediol or a mixture thereof and trioxane in a solvent containing an acid to obtain a first product;

(b) reducing said first product by dissolving said first product in a solvent and maintaining the resulting solution under a hydrogen atmosphere in the presence of a reduction catalyst to obtain a second product;

(c) alkylating said second product by maintaining said second product under a hydrogen atmosphere in the presence of a formaldehyde solution, a solvent and an alkylation catalyst to obtain a third product; and (d) quaternizing said third product by reacting said third product with a halogenated hydrocarbon in the presence of a solvent to obtain quaternary ammonium salts.

23 Claims, No Drawings

POLYMERIC QUATERNARY AMMONIUM SALTS POSSESSING ANTIMICROBIAL ACTIVITY AND METHODS FOR PREPARATION AND USE THEREOF

BACKGROUND OF THE INVENTION

The present invention relates to novel polymeric quaternary ammonium salts possessing antimicrobial activity, the use of such quaternary ammonium salts as biocidal agents, and a novel method for preparing such quaternary ammonium salts.

It is an object of the present invention to provide quaternary ammonium salts possessing a high level of antimicrobial activity against a broad spectrum of microorganisms, as compared to commercially available quaternary ammonium salts.

A further object of the present invention is to provide quaternary ammonium salts which are non-toxic to mammals.

Another object of the present invention is to provide a method for preparing such quaternary ammonium salts.

A still further object is to provide a method for killing or deactivating microbes by contacting them with the novel polymeric quaternary ammonium salts disclosed herein.

SUMMARY OF THE INVENTION

It has now been found that the foregoing and related objects are attained with the quaternary ammonium salts of the present invention.

The novel polymeric quaternary ammonium salts of this invention can be characterized by formula I:

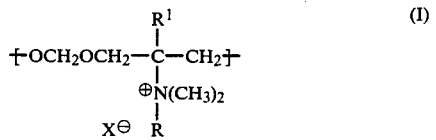

wherein R is $C_{1-20}$ alkyl, $C_{5-7}$ cycloalkyl or aralkyl, $R^1$ is methyl or ethyl and X represents a halogen.

A dioxane-derived quaternary ammonium salt characterized by formula II is a product of the same reaction by which compound I is made:

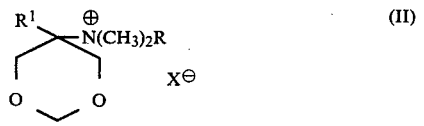

The quaternary ammonium salts characterized by formulas I and II are both prepared simultaneously in a single reaction utilizing the starting compounds, 2-nitro-2-methyl-1,3-propanediol (hereinafter sometimes called NMPD) or 2-nitro-2-ethyl-1,3-propane-diol (NEPD) and trioxane.

While both of the foregoing quaternary ammonium salts exhibit biocidal activity, the polymeric quaternary ammonium salt of formula I appears to possess a greater biocidal activity than the dioxane-derived quaternary ammonium salt of formula II. Surprisingly, however, mixtures containing varying ratios of the polymeric and dioxane-derived quaternary ammonium salts do not differ significantly in biocidal activity. This may be the result of a synergistic or potentiating effect in which one quaternary ammonium salt acts to increase the effectiveness of the other quaternary ammonium salt, contrary to the expected dilutive effect of the weaker dioxane derivative. Due to this apparent synergistic effect, there exists no need to separate out the dioxane-derived quaternary ammonium salt from the polymeric quaternary ammonium salt so as to maximize the biocidal effectiveness of the final product mixture of quaternary ammonium salts.

DETAILED DESCRIPTION OF THE INVENTION

The method for preparing the quaternary ammonium salts of the present invention comprises the steps of:
(a) initially reacting 2-nitro-2-methyl-1,3-propanediol (or NEPD) and trioxane in a solvent containing an acid to obtain a first product;
(b) reducing the first product by dissolving the first product in a solvent and maintaining the resulting solution under a hydrogen atmosphere in the presence of a reduction catalyst to obtain a second product;
(c) alkylating the second product by maintaining the second product under a hydrogen atmosphere in the presence of a formaldehyde solution, a solvent, and an alkylation catalyst to obtain a third product; and
(d) quaternizing the third product by reacting the third product with a halogenated hydrocarbon in the presence of a solvent to obtain the quaternary ammonium salts of formulas I and II.

The final product constitutes a mixture of quaternary ammonium salts of two distinct structures, polymeric and dioxane derivative. The polymeric quaternary ammonium salt is represented by Formula I, while the dioxane-derived quaternary ammonium salt is represented by Formula II.

Examples 1 and 2 illustrate one specific application of the above-described process in which a mixture of the present inventive quaternary ammonium salts can be obtained. The present invention is not to be construed as limited to these two examples.

EXAMPLE 1

2-Nitro-2-methyl-1,3-propanediol 405.00 grams (3.00 moles), 98% trioxane 92.80 grams (1.00 mole), p-toluenesulfonic acid 3.00 grams (0.016 mole), and benzene 600 ml were placed in a two liter three-necked RB flask. The flask was fitted with a thermometer, a mechanical stirrer and a Dean-Stark trap connected to a condenser. The mixture was stirred and refluxed. The slurry gradually became a homogeneous solution (usually about 30 minutes after heating started) and the benzene-water azeotrope started to distill over. Refluxing was continued until 45 ml of water was collected (i.e., approximately four hours). During this period the solution temperature was between 78° C. and 82° C. After 45 ml of water had been collected, the reaction mixture was cooled and neutralized with 3 ml triethylamine. Benzene was distilled from the clear solution first at atmospheric pressure (approximately 415 ml benzene was recovered at a solution temperature of 82° C.–100° C.) and then at about 125 mm of pressure (approximately 120 ml benzene was recovered at a solution temperature of about 48° C.–110° C.). A clear, pale-yellow, viscous liquid, 450.67 grams, containing a mixture of the reaction products polynitroformal and 5-methyl-5-nitro-1,3-dioxane was obtained as the resulting product.

REDUCTION

The crude product above was transferred to a two liter Parr high pressure reactor and dissolved in 500 ml ethanol. Raney nickel, 45 grams, was charged to this solution using approximately 100 ml ethanol for transfer and washings. The reactor vessel was closed, purged three times with hydrogen at room temperature, and pressurized to 1000 psi at 25° C. As the temperature was raised to 50° C., hydrogen absorption started. The temperature was maintained at 50° C. with a vigorous flow of cooling water and the pressure at 1000 psi. The reactor needed pressurizing every 10 minutes during which time the pressure dropped from 1000 to about 300 psi. In about 1.5 hours the total hydrogen uptake was about 4400 psi, and the temperature was then raised to 80° C. The reactor vessel was kept at 80° C. and 1200 psi for four hours to insure complete reduction. Total hydrogen uptake over the entire 5.5 hours was about 4520 psi. The reactor was then cooled to room temperature and the hydrogen vented. The reaction mixture of amine compounds was filtered and the catalyst saved. The solution of polyaminoformal and 5-methyl-5-amino, 1-3 dioxane was concentrated to about half the volume by distilling under reduced pressure (50° C. and about 125 mm of pressure).

ALKYLATION

The two-liter Parr reactor was then charged with the crude product from the reduction, 442.67 grams (5.46 moles) of 37% aqueous formaldehyde solution, about 45 grams Raney nickel catalyst (the same catalyst saved at the end of the reduction process step), and about 450 ml ethanol. The reactor was purged with hydrogen three times and pressurized to 1000 psi. The temperature was kept at 50° C. for about 30 minutes, at 100° C. for two hours, and 120° C. for 13.5 hours. Total hydrogen absorption was 3620 psi. The reactor was cooled and vented, and the solution removed. The nickel catalyst was filtered using a celite pad. The solution was concentrated at 50° C. and about 125 mm of pressure to about half its original volume. The resulting product had a light green tinge and weighed 625.96 grams. The total alkalinity of this product was found to be 4.57 meq./g. The ratio of alkylated primary, secondary, and tertiary amines in the mixture of polydimethylaminoformal and 5-dimethylamino-5-methyl-1, 3-dioxane in this material was determined to be 12.4:8.5:79. The water content, as measured by Karl-Fischer analysis, was 21% by weight.

QUATERNIZATION 598.64 grams of the aqueous ethanolic solution of the resulting product obtained from the alkylation process step described immediately above was mixed with 617.48 grams of 98% 1-bromodecane (decyl bromide) in 100 ml ethanol in a two liter RB flask and refluxed at about 78° C. The heterogenous mixture slowly turned homogeneous and pale yellow in color. Periodically (about every six hours) 0.5 grams of sample of the reaction mixture was withdrawn and treated with 10 ml heptane. This precipitated the quaternary ammonium salts, and the unreacted bromodecane was extracted into the heptane layer. The heptane layer was analyzed by a gas chromatograph for bromodecane and the amounts of unreacted bromodecane were back-calculated in order to determine the extent of the quaternization. After 56 hours of refluxing, the reaction was stopped to obtain 1266.44 grams of a clear, orange-yellow, viscous liquid.

10.0038 grams of this solution was placed in a RB flask under vacuum (0.25 mm pressure and 65° C.) to distill off all volatiles. The resulting product was 7.4507 grams of a pale yellow solid, a mixture of the quaternary ammonium salts I and II of the present invention. The liquid product therefore was determined to consist of 74.51% solids and 5.20% unreacted bromodecane.

EXAMPLE 2

Example 1 was substantially repeated. Example 2 utilized the same starting materials as Example 1 in the same amounts, except the total time of reaction for the initial reaction was about four hours (as opposed to 4.5 hours in Example 1). 448.87 grams of a clear, pale-yellow, viscous liquid was obtained as the resulting product.

The reduction reaction involving the resulting product was the same as that of Example 1, except that the total hydrogen uptake was about 4500 psi (as opposed to about 4520 psi in Example 1).

The alkylation reaction involving the reduction product was the same as that of Example 1, with a total hydrogen uptake of about 4040 psi (as opposed to 3620 psi in Example 1). The resulting product weighed 580.35 grams. The total alkalinity of the resulting product was found to be 4.64 meg/g. The ratio of primary, secondary, and tertiary amines in the resulting product was determined to be 6.2:8.4:85.4. The water content, as measured by Karl-Fischer analysis, was 22% by weight.

367.46 grams of the aqueous ethanolic solution of the alkylation product was mixed with 384.83 grams of 98% 1-bromodecane (decyl bromide) in 70 ml ethanol in a two liter RB flask and refluxed at about 78° C. As in Example 1, solution samples were periodically tested to determine the extent of quaternization. After 56 hours of refluxing, the reaction was stopped to obtain 791.53 grams of a liquid product, a mixture of the quaternary salts I and II. The product was analyzed and determined to contain 72.41% solids and 3.35% unreacted bromodecane.

The biocidal activity evaluations of the present invention quaternary ammonium salts and mixtures thereof as well as of commercially available biocides (for comparison purposes) were conducted using the Dynatech MIC-2000 system (available from Dynatech Laboratories, Inc., Alexandria, Va.). The Dynatech MIC-2000 system provides a quantitative factor, namely the specific concentration of the compound that inhibits the growth of a test organism.

All compounds were prepared for testing by initially making a 1.0% w/v solution. These were then serially diluted so as to yield concentrations of sample in a range of 2000–16 mg/l. Testing was carried out under aseptic conditions in Trypticase Soy Broth (BBL, Div. Becton, Dickinson & Co., Cockeysville, MD). Each test was performed in duplicate and run at pH levels of 7.0, 8.0, and 9.0. The pH of the test medium was adjusted by the addition of 10% w/v NaOH before sterilization.

Organisms utilized for MIC testing were all purchased from the American Type Culture Collection (ATCC), Rockville, MD. The six organisms chosen for these tests were:

1. *Staphylococcus aureus* ATCC 6538 (Gram-positive), referred to hereafter as Sa.

2. *Pseudomonas aeruginosa* ATCC 15442 (Gram-negative), referred to hereafter as $Pa_1$.
3. *Pseudomonas aeruginosa* ATCC 10145 (Gram-negative), referred to hereafter as $Pa_2$.
4. *Klebsiella pneumoniae* ATCC 13883 (Gram-negative), referred to hereafter as Kp.
5. *Escherichia coli* ATCC 8739 (Gram-negative), referred to hereafter as Ec.
6. *Proteus Mirabilis* ATCC 4675 (Gram-negative), referred to hereafter as Pm.

Inocula were prepared in Brain Heart Infusion Broth (BHI, Difco Laboratories, Detroit, MI), and standardized to $3.0 \times 10^8$ CFU/ml in 0.85% sterile saline. Each test system was automatically inoculated with 0.0015 ml of inoculum, so as to give a final inoculum concentration of $4.0 \times 10^5$ CFU/ml. Incubation of test systems was carried out at $37° \pm 2°$ C. for 18 hours. Plates were read and evaluated at this time, and results reported in mg/l of compound that inhibited the growth of the test organisms.

Bioactivity data against various organisms of the final products containing mixtures of the present inventive quaternary ammonium salts obtained from Examples 1 and 2 is presented in Table 1. The present inventive quaternary ammonium salts possess a high level of biocidal activity against a broad-spectrum of microorganisms.

TABLE 1

Bioactivity of Mixtures of Present Inventive Quaternary Ammonium Salts[1]

| Sample | pH | Sa | $Pa_1$ | $Pa_2$ | Kp | Ec | Pm |
|---|---|---|---|---|---|---|---|
| Example 1 | 7 | <16 | 63–32 | 63–32 | 63–32 | <16 | >2000–1000 |
| | 8 | <16 | 63–32 | 63–32 | 63–32 | <16 | 1000–500 |
| | 9 | <16 | 63–32 | 63–32 | 32–16 | <16 | 500–250 |
| Example 2 | 7 | <16 | 63–32 | 63–32 | 63–32 | <16 | >2000 |
| | 8 | <16 | 63–32 | 63–32 | 32–16 | <16 | >2000–1000 |
| | 9 | <16 | 63–32 | 63–32 | 32–16 | <16 | 500–250 |

[1] MIC Values (ppm)
[2] Sa: *Staphylococcus aureus*
$Pa_1$: *Pseudomonas aeroginosa* 15442
$Pa_2$: *Pseudomonas aeroginosa* 10145
Kp: *Klebsiella pneumoniae*
Ec: *Escherichia coli*
Pm: *Proteus mirabilis*

Although the initial reaction solvent utilized in Examples 1 and 2 constituted benzene, other solvents can also be used. The initial reaction solvent utilized appears to affect the course of the initial reaction between 2-nitro-2-methyl-1,3-propanediol and trioxane so as to vary the proportion of polynitroformal to 5-methyl-5-nitro-1,3-dioxane (and thus in the end to vary the proportion of the polymeric quaternary ammonium salt to the dioxane-derived quaternary ammonium salt in the final product). Various initial reaction solvents and the effect of those solvents on the reaction of 2-nitro-2-methyl-1,3-propanediol and trioxane are presented in Table 2.

TABLE 2

Initial Reaction Solvent Effects

| Solvent | Temperature (°C.) | Major Product |
|---|---|---|
| Water | 100 | dioxane derivative |
| Benzene | 80 | polymer |
| Toluene | 85 | polymer and dioxane derivative |
| Cyclohexane | 110 | dioxane derivative |
| | 81 | dioxane derivative |

Although p-toluenesulfonic acid was used as the initial reaction source of hydrogen ions in Examples 1 and 2, any suitable acid could also be used.

The solvent used in the reduction, alkylation, and quaternization process steps in Examples 1 and 2 was ethanol. Other suitable solvents include other alcohols such as methanol. Further, the reduction, alkylation, and quaternization solvents need not be identical. For example, the initial reaction or first product is soluble in alcohols, DMF, chloroform, and acetone. The reduction or second product is soluble in water, alcohols, DMF, acetone, and chloroform. The alkylation or third product is soluble in cold water, alcohols, ether, and chloroform.

In Examples 1 and 2, the reduction catalyst was saved and reused as the alkylation catalyst. Such a reuse lends itself to a combined reduction-alkylation process step. Of course, the method for preparing quaternary ammonium salts of the present invention does not require the reuse of the reduction catalyst as the alkylation catalyst. Indeed, two different catalysts can be utilized, and neither of the catalysts need be the Raney nickel catalyst utilized in Examples 1 and 2, but rather any suitable catalyst(s) can be used.

The formaldehyde solution utilized in Examples 1 and 2 was an aqueous formaldehyde solution. A methanolic solution of formaldehyde (Methyl Form-Cell available from the Celanese Corporation) can be used instead of the aqueous formaldehyde solution. Such a substitution may increase the catalyst life in the alkylation reaction.

Although 1-bromodecane was used in Examples 1 and 2 as the halogenated hydrocarbon in the quaternization reaction step, other suitable halogenated hydrocarbons include ethyl bromide, benzyl chloride, methyl iodide, propyl bromide, hexyl bromide, octyl bromide, dodecyl bromide, and hexadecyl bromide.

It has been found that iodide compounds generally appear to react faster than bromide compounds, which in turn generally appear to react faster than chloride compounds.

The group R, when an alkyl group, may vary from $C_1$ to $C_{20}$, preferably from $C_2$ to $C_{12}$, and may include cycloalkyls having from 5 to 7 carbon atoms. It may also be an aralkyl group such as benzyl or toluyl. The length of the alkyl group attached to the nitrogen atom of the quaternary ammonium salt appears to affect the bioactivity of the salt. Table 3 presents data on the bioactivity of reaction product mixtures of the present inventive quaternary ammonium salts prepared utilizing various alkyl bromides as quaternization compounds. As the alkyl chain length increases, the bioactivity of the resulting quaternary ammonium salts increases. This trend, however, appears to peak at about the $C_{12}$ alkyl group; e.g., the dodecyl bromide salt ($C_{12}$) exhibits a lower bioactivity than the decyl bromide salt ($C_{10}$).

TABLE 3

Bioactivity of Mixtures of Present Inventive Quaternary Ammonium Salts Prepared Utilizing Various Alkyl Bromides as Quaternization Agents

| Quaternization Compound Used | ph | Sa | Pa$_1$ | Pa$_2$ | Kp | Ec | Pm |
|---|---|---|---|---|---|---|---|
| C$_3$H$_7$Br | 7 | >2000 | >2000 | >2000 | >2000 | >2000 | >2000 |
|  | 8 | >2000 | >2000 | >2000 | >2000 | >2000 | >2000 |
|  | 9 | 63–125 | >2000 | >2000 | 125–250 | 250–500 | >2000 |
| C$_6$H$_{13}$Br | 7 | 125–250 | 250–500 | 500–1000 | 250–500 | 125–250 | >2000 |
|  | 8 | 32–63 | 125–250 | 500–1000 | 63–125 | 63–125 | >2000 |
|  | 9 | <16 | 13–16 | 63–125 | <16 | <16 | 500–1000 |
| C$_8$H$_{17}$Br | 7 | 32–63 | 16–32 | 32–63 | 32–63 | 16–32 | 250–500 |
|  | 8 | <16 | 16–32 | 16–32 | 16–32 | <16 | 125–500 |
|  | 9 | <16 | <16 | <16 | <16 | <16 | 63–125 |
| C$_{10}$H$_{21}$Br | 7 | <16 | <16 | 16–32 | <16 | <16 | 250–500 |
|  | 8 | <16 | <16 | <16 | <16 | <16 | 125–250 |
|  | 9 | <16 | <16 | <16 | <16 | <16 | 63–125 |
| C$_{12}$H$_{25}$Br | 7 | <16 | 16–32 | 32–63 | <16 | <16 | 500–1000 |
|  | 8 | <16 | 16–32 | 32–63 | <16 | <16 | 250–500 |
|  | 9 | <16 | 16–32 | 32–63 | <16 | <16 | 32–63 |

For long chain alkyl bromides (C$_6$ or above), it was found that ethanol was a better solvent than methanol. This was apparently due to the higher boiling point of ethanol (and thus the higher reaction temperature) and the lower reactivities of the long chain alkyl bromides.

Although a single halogenated hydrocarbon was used as the quaternization agent in Example 1 and 2, a mixture of halogenated hydrocarbons can also be used. The bioactivities of the present inventive quaternary ammonium salts prepared utilizing various quaternization compounds and mixtures thereof are presented in Table 4.

TABLE 4

Bioactivity of Mixtures of Present Inventive Quaternary Ammonium Salts Prepared Utilizing Various Quaternization Compounds

| Quaternization Compound Used Mol Percent | pH | Sa | Pa$_1$ | Pa$_2$ | Kp | Ec | Pm |
|---|---|---|---|---|---|---|---|
| 100% Benzyl | 7 | 2000–1000 | >2000 | >2000 | 2000–1000 | 500–250 | >2000 |
|  | 8 | 1000–500 | 2000–1000 | 2000–1000 | 1000–500 | 250–125 | >2000 |
|  | 9 | 250–125 | 1000–500 | 1000–500 | 125–63 | 125–63 | >2000 |
| Benzyl Chloride 50% | 7 | 125–250 | 250–500 | 500–1000 | 250–500 | 125–250 | >2000 |
|  | 8 | 32–63 | 125–250 | 500–1000 | 63–125 | 63–125 | >2000 |
| Bromodecane: 50% | 9 | 63–32 | 125–63 | 125–63 | 126–63 | 63–32 | 1000–500 |
| 100% Bromodecane | 7 | 32–63 | 63–32 | 63–32 | 63–32 | 32–16 | 2000–1000 |
|  | 8 | 32–16 | 32–16 | 63–32 | 32–16 | <16 | 1000–500 |
|  | 9 | <16 | <16 | 32–16 | <16 | <16 | 500–250 |
| 100% Bromoethane | 7 | 1000–500 | >2000 | >2000 | 2000–1000 | 1000–500 | >2000 |
|  | 8 | 1000–500 | 2000–1000 | 2000–1000 | 2000–1000 | 1000–500 | >2000 |
|  | 9 | 1000–500 | >2000 | >2000 | 100–500 | 1000–500 | >2000 |
| Bromodecane: 50% Bromoethane: 50% | 7 | 63–32 | 125–63 | 125–63 | 125–630 | 63–32 | >2000 |
|  | 8 | 32–16 | 63–32 | 125–63 | 63–32 | 32–16 | 2000–1000 |
|  | 9 | <16 | 125–63 | 63–32 | 32–16 | <16 | 500–250 |
| Bromodecane: 75% Bromoethane: 25% | 7 | 500–250 | 1000–500 | 2000–1000 | 1000–500 | 500–250 | >2000 |
|  | 8 | 500–250 | 1000–500 | 2000–1000 | 1000–500 | 500–250 | >2000 |
|  | 9 | 250–125 | 100–500 | 100–500 | 500–250 | 500–250 | >2000 |
| Bromodecane: 25% Bromoethane: 75% | 7 | 250–125 | 500–250 | 500–250 | 500–250 | 250–125 | >2000 |
|  | 8 | 125–63 | 250–125 | 250–125 | 250–125 | 125–63 | >2000 |
|  | 9 | 63–32 | 250–125 | 250–125 | 125–63 | 63–32 | 2000–1000 |

The molecular weight of the polymeric quaternary ammonium salt appears to depend on the relative amounts of 2-nitro-2-methyl-1-3-propanediol and trioxane used in the initial reaction. Generally, as the mol ratio of 2-nitro-2-methyl-1-3-propanediol to trioxane increased, the molecular weight of the resulting polymeric quaternary ammonium salt increased.

The reaction scheme outlined above results in the formation of both the polymeric and dioxane-derived quaternary ammonium salts simultaneously. The polymeric quaternary ammonium salt is the product of a linear-chain formation and as such is a kinetic product, while the dioxane derivative quaternary ammonium salt is the product of cyclization, and thus constitutes a thermodynamic product. Higher temperature and long reaction times, therefore, favor the formation of the dioxane-derived quaternary ammonium salt.

Aside from varying the reaction conditions, the ratio of the two quaternary ammonium salts in the final product can also be affected through the use of separation techniques at appropriate points in the reaction scheme. For example, the dioxane-derived product after the initial reaction of the starting compounds can be removed from the product by washing with hot water. Also, due to the difference in boiling points between the polymeric and dioxane-derived products resulting after the alkylation process step, the dioxane-derived product can be removed by vacuum distillation. Thus, using one or both of these separation techniques, a final product can be obtained containing primarily the polymeric quaternary ammonium salt or the dioxane-derived quaternary ammonium salt or mixtures containing varying proportions of the two quaternary ammonium salts.

As can be seen from Table 5, the polymeric quaternary ammonium salt (I) exhibits a greater biocidal activity than the dioxane-derived quaternary ammonium salt (II).

TABLE 5

Bioactivity of Individual Present Inventive Quaternary Ammonium Salts

| Compound | pH | Sa | Pa$_1$ | Pa$_2$ | Kp | Ec | Pm |
|---|---|---|---|---|---|---|---|
| II | 7 | >2000 | >2000 | >2000 | >2000 | >2000 | >2000 |
|  | 8 | 500–1000 | >2000 | >2000 | 1000–2000 | 1000–2000 | >2000 |
|  | 9 | 63–125 | >2000 | >2000 | 500–1000 | 250–500 | >2000 |
| I | 7 | 32–63 | 16–32 | 32–63 | 32–63 | 16–32 | 250–500 |
|  | 8 | <16 | 16–32 | 16–32 | 16–32 | <16 | 125–250 |
|  | 9 | <16 | <16 | <16 | <16 | <16 | 63–125 |

The presence of the dioxane-derived quaternary ammonium salt, however, does not appear to affect the activity of the polymeric quaternary ammonium salt. This could be the result of a synergistic effect in which one salt increases the activity of the other salt. The separation of the dioxane-derived products from the polymeric products, therefore, is not necessary in order to prepare a more active product.

Table 6 contains data on biocidal activity for four samples, A through D, with respectively increasing amounts of the dioxane-derived quaternary ammonium salt as compared to the polymeric quaternary ammonium salt. Sample A was prepared by washing the initial reaction product with hot water to remove the dioxane-derived product and by vacuum distilling the alkylation product to remove the dioxane-derived product. Sample B was prepared by simply washing the initial reaction product with hot water to remove the dioxane-derived product. Sample C was prepared by simply vacuum distilling the alkylation reaction product to remove the dioxane-derived component. Sample D was prepared using the method for preparing the quaternary ammonium salts of the present invention without modifying such with any separation techniques.

The biocidal activity of Samples A–D are presented in Table 6. As can be seen from an examination of Table 6, Samples A–D all exhibit similar biocidal activity despite the differences in the relative amounts of the polymeric and dioxane-derived quaternary ammonium salts in the final product.

TABLE 6

Bioactivity of Various Mixtures of the Present Inventive Quaternary Ammonium Salts

| Sample[1] | pH | Sa | Pa$_1$ | Pa$_2$ | Kp | Ec | Pm |
|---|---|---|---|---|---|---|---|
| A | 7 | <16 | 32–16 | 32–16 | 63–16 | <16 | 500–250 |
|  | 8 | <16 | 63–32 | 63–32 | 63–32 | <16 | 1000–500 |
|  | 9 | <16 | 63–32 | 63–32 | 32–16 | <16 | 250–125 |
| B | 7 | 32–16 | 32–16 | 63–32 | 63–32 | <16 | 500–250 |
|  | 8 | 32–16 | 63–32 | 63–32 | 63–32 | <16 | 500–250 |
|  | 9 | <16 | 32–16 | 32–16 | <16 | <16 | 250–125 |
| C | 7 | <16 | 63–32 | 63–32 | 32–16 | <16 | >2000 |
|  | 8 | <16 | 63–32 | 63–32 | 32–16 | <16 | 1000–500 |
|  | 9 | <16 | 63–32 | 63–32 | 32–16 | <16 | 250–125 |
| D | 7 | <16 | 32–16 | 63–32 | 32–16 | <16 | 1000–500 |
|  | 8 | <16 | 32–16 | 63–32 | 63–32 | <16 | 500–250 |
|  | 9 | <16 | 63–32 | 63–32 | 32–16 | <16 | 250–125 |

[1]Ratio of polymeric to dioxane derivative quaternary ammonium salts decreases in the order: A–B–C–D.

The biocidal activity of a mixture of the present inventive quaternary ammonium salts was tested over a five month period, and it was found that there was no appreciable loss in biocidal activity over that period of time.

The acute toxicity of a mixture of the present inventive quaternary ammonium salts was tested using the final product from Example 1 diluted to give a 10% (by weight) solution in water. The results of the toxicity tests are given in Table 7.

TABLE 7

Acute Toxicity of Example 1 Final Product

| Test | Species | Results | Remarks |
|---|---|---|---|
| Oral LD$_{50}$ | Rat | >6000 mg/kg | Nontoxic |
| Eye Irritation | Rabbit | Score 35.7 at 24 h | Irritant |
| Skin Irritation | Rabbit | Score 3.4 | Irritant |
| Skin Corrosion | Rabbit | No tissue damage | Non corrosive |

Three commercially available quaternary ammonium salts were compared with the quaternary ammonium salts prepared in accordance with the present invention. The three commercially available compounds consisted of Buckman WSCP and WSCP II and Roccal. Two other commercially available biocides were also tested, CS-1135 and Bronopol.

The polymeric quaternary ammonium salts of the present invention and mixtures of the polymeric and dioxane-derived quaternary ammonium salts possess both a higher level of biocidal activity and a broader spectrum activity as compared to the commercially available quaternary ammonium salts and even the oxazolidine CS-1135. Although Bronopol was more active than the quaternary ammonium salts of the present invention, Bronopol possesses several disadvantages which the present inventive quaternary ammonium salts do not possess, namely Bronopol involves the slow release of formaldehyde and possible nitrite formation which is known to be a precursor for the nitrosoamines which are suspected carcinogens. The present inventive quaternary ammonium salts exhibit high biocidal activity without possessing these disadvantages.

While several forms and aspects of the invention have been illustrated in detail herein, the invention is not intended to be limited to only those embodiments. Rather, persons skilled in the art will see other embodiments that are apparent to them and all such are intended to be included herein to the extent that they are embraced by the appended claims.

I claim:
1. The polymeric quaternary ammonium salt have the formula I:

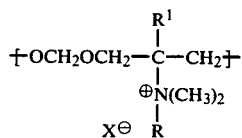 (I)

wherein R is $C_{1-20}$ alkyl, $C_{5-7}$ cycloalkyl or aralkyl group, $R^1$ is methyl or ethyl and X is a halogen atom.

2. The quaternary ammonium salt as claimed in claim 1, wherein R is a $C_{1-20}$ alkyl group.

3. The quaternary ammonium salt as claimed in claim 1, wherein R is an aralkyl group.

4. The quaternary ammonium salt as claimed in claim 2, wherein R is an ethyl group.

5. The quaternary ammonium salt as claimed in claim 2 wherein R is a benzyl group.

6. The quaternary ammonium salt as claimed in claim 2 wherein R is a decyl group.

7. The quaternary ammonium salt as claimed in claim 1 wherein $R^1$ is methyl.

8. The quaternary ammonium salt as claimed in claim 1 wherein $R^1$ is ethyl.

9. The method of preparing polymeric quaternary ammonium salts comprising the steps of:
  (a) initially reacting 2-nitro-2-methyl-1,3-propanediol or 2-nitro-2-ethyl-1,3-propanediol or a mixture thereof and trioxane in a solvent containing an acid to obtain a first product;
  (b) reducing said first product by dissolving said first product in a solvent and maintaining the resulting solution under a hydrogen atmosphere in the presence of a reduction catalyst to obtain a second product;
  (c) alkylating said second product by maintaining said second product under a hydrogen atmosphere in the presence of a formaldehyde solution, a solvent and an alkylation catalyst to obtain a third product; and
  (d) quaternizing said third product by reacting said third product with a halogenated hydrocarbon in the presence of a solvent to obtain quaternary ammonium salts.

10. The method of preparing quaternary ammonium salts as claimed in claim 9, wherein the initial reaction solvent is benzene, toluene, or a mixture thereof.

11. The method of preparing quaternary ammonium salts as claimed in claim 9, wherein the solvents used in the reducing, alkylating, and quaternizing steps are the same solvent selected from the group consisting of methanol and ethanol.

12. The method of preparing quaternary ammonium salts as claimed in claim 9, wherein the acid is p-toluenesulfonic acid.

13. The method of preparing quaternary ammonium salts as claimed in claim 9, wherein the reduction catalyst or the alkylation catalyst comprises Raney nickel.

14. The method of preparing quaternary ammonium salts as claimed in claim 9, wherein the formaldehyde solution is an aqueous or methanolic formaldehyde solution.

15. The method of preparing quaternary ammonium salts as claimed in claim 9, wherein the halogenated hydrocarbon is decyl bromide, ethyl bromide, benzyl chloride, or a mixture thereof.

16. The method of preparing quaternary ammonium salts as claimed in claim 9, wherein the initial reaction is conducted at a temperature of about 78° C. to 85° C.

17. The method of preparing quaternary ammonium salts as claimed in claim 9, wherein the reduction reaction is conducted at a temperature of about 50° C. to 80° C. and under a hydrogen pressure of about 1000 psi to 1200 psi.

18. The method of preparing quaternary ammonium salts as claimed in claim 9, wherein the alkylation reaction is conducted at a temperature of about 50° C. to 120° C. and under a hydrogen pressure of about 1000 psi.

19. The method of preparing quaternary ammonium salts as claimed in claim 9, wherein the product of step (a) comprises a mixture of polynitroformal and 5-methyl-5-nitro-1,3-dioxane.

20. The method of preparing quaternary ammonium salts as claimed in claim 9, wherein the product of step (a) comprises a mixture of polynitroformal and 5-ethyl-5-nitro-1,3-dioxane.

21. The method of preparing quaternary ammonium salts as claimed in claim 9, wherein the product of step (b) comprises a mixture of polyaminoformal and 5-ethyl-5-amino-1,3-dioxane.

22. The method of preparing quaternary ammonium salts as claimed in claim 9, wherein the product of step (c) comprises a mixture of polydimethylaminoformal and 5-ethyl-5-dimethylamino-1,3-dioxane.

23. The method of preparing quaternary ammonium salts as claimed as claim 9, wherein the quaternary ammonium salts comprise a mixture of a compound having the formula I:

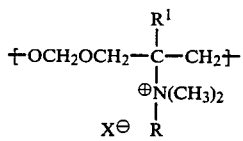 (I)

and a compound of formula II:

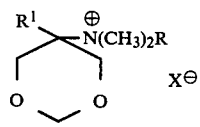 (II)

wherein R is $C_{1-20}$ alkyl, $C_{5-7}$ cycloalkyl or aralkyl group, $R^1$ is methyl or ethyl, and X is a halogen.

* * * * *

UNITED STATES PATENT AND TRADEMARK OFFICE
CERTIFICATE OF CORRECTION

PATENT NO. : 4,567,302

DATED : January 28, 1986

INVENTOR(S) : Kallidaikurichi N. Sivaramakrishnan

It is certified that error appears in the above-identified patent and that said Letters Patent is hereby corrected as shown below:

On title page, insert Assignee:

--[73] Angus Chemical Company--

Signed and Sealed this

Twentieth Day of May 1986

[SEAL]

Attest:

DONALD J. QUIGG

Attesting Officer

Commissioner of Patents and Trademarks